(12) United States Patent
Smith et al.

(10) Patent No.: US 8,740,832 B2
(45) Date of Patent: Jun. 3, 2014

(54) OSTOMY BAG

(75) Inventors: Rory James Maxwell Smith, West Sussex (GB); Paul Bird, West Sussex (GB); Owen May, West Sussex (GB)

(73) Assignee: Welland Medical Limited, Crawley, West Sussex (GB)

( * ) Notice: Subject to any disclaimer, the term of this patent is extended or adjusted under 35 U.S.C. 154(b) by 1332 days.

(21) Appl. No.: 12/522,509

(22) PCT Filed: Jan. 22, 2007

(86) PCT No.: PCT/GB2007/000186
§ 371 (c)(1),
(2), (4) Date: Nov. 18, 2010

(87) PCT Pub. No.: WO2007/085803
PCT Pub. Date: Aug. 2, 2007

(65) Prior Publication Data
US 2011/0238024 A1    Sep. 29, 2011

(30) Foreign Application Priority Data
Jan. 24, 2006 (GB) .................................. 0601379.1

(51) Int. Cl.
*A61M 5/00* (2006.01)
*A61F 5/445* (2006.01)
*A61F 5/448* (2006.01)
*A61F 5/44* (2006.01)

(52) U.S. Cl.
CPC .................. *A61F 5/445* (2013.01); *A61F 5/448* (2013.01); *A61F 2005/4402* (2013.01)
USPC .......................................................... 604/8

(58) Field of Classification Search
USPC .......................................................... 604/336
See application file for complete search history.

(56) References Cited

U.S. PATENT DOCUMENTS

| 4,078,568 A | * | 3/1978 | Etes et al. ...................... 604/336 |
| 4,403,991 A | * | 9/1983 | Hill ................................ 604/337 |
| 4,411,659 A | * | 10/1983 | Jensen et al. .................. 604/332 |
| 4,465,486 A | * | 8/1984 | Hill ................................ 604/337 |
| 4,559,048 A | * | 12/1985 | Steer .............................. 604/338 |
| 4,755,177 A | * | 7/1988 | Hill ................................ 604/336 |
| 4,828,553 A | * | 5/1989 | Nielsen .......................... 604/339 |
| 5,248,308 A | * | 9/1993 | von Emster .................... 604/337 |

(Continued)

*Primary Examiner* — Susan Su
*Assistant Examiner* — Guy K Townsend
(74) *Attorney, Agent, or Firm* — Heslin Rothenberg Farley & Mesiti P.C.

(57) ABSTRACT

The invention provides a drainage bag assembly for receiving bodily waste; the drainage bag assembly comprising outer (6) and inner (12) bags secured to one side of a flange (2), the flange (2) being provided with means defining an orifice to 5 enable bodily waste to be received by the inner bag (12), and the flange (2) having connected to an opposite side thereof means for securing the drainage bag assembly to the body of a patient; the outer bag (6) being detachably secured by means of a peelable but non-repositionable adhesive to a first attachment zone (4) on the flange and the inner bag being detachably secured by means of a peelable adhesive to a 0 second attachment zone (16) on the flange, wherein the first attachment zone (4) surrounds the second attachment zone (16) and is non-overlapping therewith; and the second attachment zone (16) surrounds the means defining the orifice; and wherein the outer bag (6) can be removed or opened to permit access to the interior thereof and removal of the inner bag (12).

23 Claims, 4 Drawing Sheets

(56) References Cited

U.S. PATENT DOCUMENTS

| | | | | |
|---|---|---|---|---|
| D369,662 S | * | 5/1996 | Kuentz | D24/127 |
| 5,549,587 A | * | 8/1996 | Norton | 604/333 |
| D377,115 S | * | 1/1997 | Feriend et al. | D24/117 |
| 5,591,144 A | * | 1/1997 | Smith et al. | 604/327 |
| 5,607,412 A | * | 3/1997 | Brown | 604/332 |
| 5,759,180 A | * | 6/1998 | Myhres | 604/332 |
| 5,776,120 A | * | 7/1998 | Shelley et al. | 604/339 |
| 5,843,054 A | * | 12/1998 | Honig | 604/345 |
| 5,912,059 A | * | 6/1999 | Jones et al. | 428/35.2 |
| 5,938,647 A | * | 8/1999 | Smith | 604/332 |
| 5,989,235 A | * | 11/1999 | Quacquarella et al. | 604/332 |
| 6,135,986 A | * | 10/2000 | Leisner et al. | 604/322 |
| 6,186,989 B1 | * | 2/2001 | Horie | 604/345 |
| 7,073,309 B2 | * | 7/2006 | van Driesten | 53/415 |
| 7,090,664 B2 | * | 8/2006 | Holter | 604/332 |
| 7,214,217 B2 | * | 5/2007 | Pedersen et al. | 604/333 |
| 7,306,581 B2 | * | 12/2007 | Falconer et al. | 604/332 |
| 7,604,622 B2 | * | 10/2009 | Pedersen et al. | 604/333 |
| 8,211,072 B2 | * | 7/2012 | Smith et al. | 604/342 |
| 2004/0049837 A1 | * | 3/2004 | Falconer et al. | 4/144.1 |
| 2004/0059306 A1 | * | 3/2004 | Tsal et al. | 604/332 |
| 2005/0070863 A1 | * | 3/2005 | Bulow et al. | 604/332 |
| 2005/0075616 A1 | * | 4/2005 | Holter | 604/332 |
| 2005/0085779 A1 | * | 4/2005 | Poulsen et al. | 604/332 |
| 2005/0143696 A1 | * | 6/2005 | Pedersen et al. | 604/332 |
| 2005/0159717 A1 | * | 7/2005 | Holtermann | 604/332 |
| 2007/0219514 A1 | * | 9/2007 | Strobech | 604/336 |
| 2008/0226864 A1 | * | 9/2008 | Willis et al. | 428/98 |
| 2008/0306459 A1 | * | 12/2008 | Albrectsen | 604/333 |
| 2011/0054425 A1 | * | 3/2011 | Smith et al. | 604/342 |

* cited by examiner

OSTOMY BAG

CROSS REFERENCE TO RELATED APPLICATIONS

This application is a national phase filing under 35 U.S.C. §371 of PCT International Application PCT/GB2007/000186, filed Jan. 22, 2007, and published under PCT Article 21(2) in English as WO 2007/085803 A1 on Aug. 2, 2007. PCT/GB2007/000186 claimed priority from British application No. 0601379.1 filed on Jan. 24, 2006. The entire contents of the prior applications are incorporated herein by reference.

This invention relates to drainage bag assemblies, such as ostomy bags, for receiving bodily waste, and more particularly to an ostomy bag containing a removable inner liner.

BACKGROUND OF THE INVENTION

Ostomy bags for receiving bodily waste from colostomy and ileostomy patients are well known. One of the problems faced by users of ostomy bags, particularly colostomy bags, is how to dispose of the contents of the bag.

Many known forms of ostomy bag are made from materials that are not biodegradable and are not easily flushed down a W.C. because of, for example, the buoyancy and relative bulk of the bags. With non-flushable bags, it has been common practice to cut an edge of the bag and then deposit the contents of the bag in the W.C. for flushing away, leaving the soiled bag for separate disposal, e.g. by incineration or by wrapping and placing in a waste bin.

One solution to this problem has been to provide ostomy bags made from materials that are capable of being flushed down a W.C. and examples of such bags are disclosed in WO 94/12128, EP 0259184, US 2004/0059306, EP 0320895, U.S. Pat. No. 5,989,235, GB 2083762, EP 388924, GB 2227668 and GB 2193925.

In many cases, the flushable ostomy bag comprises an inner bag which is formed from a material that disintegrates or dissolves in water or is otherwise disposable and a protective outer bag formed from a material that is resistant to water. The outer bag can be constructed so as to be reusable several times, means being provided for opening the outer bag to permit removal and replacement of the inner bag or liner. The outer and inner bags may both be attached, directly or indirectly, to an adhesive flange which comprises a layer of a bio-compatible adhesive such as a hydrocolloid adhesive to secure the ostomy bag to the body of the patient about the stomal opening.

US 2004/0059306 in particular describes several forms of construction of two piece ostomy bags in which the inner bag or liner is replaceable and a re-fastenable opening is provided in the outer bag to give access to the inner bag so that it can be replaced.

U.S. Pat. No. 5,785,695 (Alcare) discloses ostomy appliances comprising inner and outer bags that are releasably attached to an adhesive flange by means of mechanical couplings comprising coupling rings having annular grooves that engage corresponding annular rims on the adhesive flange to form snap-fit connections.

US 2003/0153883 (Hansen) discloses ostomy appliances comprising an adhesive flange to which is secured a first mechanical coupling ring for the attachment of an outer bag. An inner bag or liner can also be secured to the first mechanical coupling ring by means of a second mechanical coupling ring which encircles the mouth of the inner bag and which forms a snap-fit connection against the radially inner surface of the first mechanical coupling ring.

A problem with ostomy appliances employing coupling rings to connect the inner and outer bags to an adhesive flange is that the coupling rings almost invariably make the appliance stiffer and less flexible and hence less comfortable to wear. In addition, where the coupling rings for the inner and outer bags are placed relatively close together, this can make separation and replacement of the bags difficult, particularly for people with impaired or reduced manual dexterity. A further problem with using coupling rings is that they will need to be removed prior to disposal of an inner bag down a WC. Not only does this add an additional potentially awkward step to the removal and disposal process but it may also result in the user's hands coming into contact with faecal waste at the mouth of the bag.

As an alternative to using mechanical couplings, adhesive bonding has been used to secure the inner and outer bags to the adhesive flange. Examples of ostomy bags making use of adhesive bonding can be found in U.S. Pat. No. 5,865,819 (Hollister) and WO 2004/082452 (Coloplast).

U.S. Pat. No. 5,865,819 discloses an arrangement in which the inner and outer bags each have their own separate adhesive flange for direct connection to the body of the patient.

WO 2004/082452 discloses ostomy bags comprising an adhesive flange for attachment to the body of a patient, and inner and outer bags. The inner and outer bags are each provided with adhesive rings for attachment to the adhesive flange. In the preferred ostomy bag constructions disclosed in WO 2004/082452, the outer diameter of the adhesive ring of the inner bag is larger than the inner diameter of the adhesive ring of the outer bag and hence there is overlap between the two adhesive rings.

SUMMARY OF THE INVENTION

The present invention provides a drainage bag assembly for receiving bodily waste; the drainage bag assembly comprising outer and inner bags secured to one side of a flange, the flange being provided with means defining an orifice to enable bodily waste to be received by the inner bag, and the flange having connected to an opposite side thereof means for securing the drainage bag assembly to the body of a patient; the outer bag being detachably secured by means of a peelable but non-repositionable adhesive to a first attachment zone on the flange and the inner bag being detachably secured by means of a peelable adhesive to a second attachment zone on the flange, wherein the first attachment zone surrounds the second attachment zone and is non-overlapping therewith; and the second attachment zone surrounds the means defining the orifice; and wherein the outer bag can be removed or opened to permit access to the interior thereof and removal of the inner bag.

Particular and preferred embodiments of the invention are as set out in the claims appended hereto or in the paragraphs below.

The outer bag is secured to the adhesive flange by means of a peelable but non-repositionable adhesive to a first attachment zone on the flange. The term "non-repositionable" as used herein means that once the outer bag has been peeled away from the first attachment zone, it is not possible to reattach it to the first attachment zone by finger pressure alone. Thus, the adhesive is one which does not retain any adhesive capability at ambient temperature after the two surfaces to which it is bonded have been peeled apart.

The peelable non-repositionable adhesive can be a hot-melt adhesive. The hot-melt adhesive can be a thermoplastic polymer that has a lower melting point than the two items that it is intended to join. Thus, where the adhesive flange comprises a layer of adhesive such as a hydrocolloid adhesive carried on a backing sheet, and the backing sheet comprises a layer formed from a first polymer, the thermoplastic polymer constituting the hot-melt adhesive will be one which has a lower melting point than the said first polymer. Typically, the difference in melting points between the first polymer and the hot-melt adhesive will be of the order of at least 20° C.

Similarly, the hot-melt adhesive will have a melting point which is lower (e.g. by 20° C. or more) than the melting point of the polymer from which the outer bag is formed. Where the wall of the outer bag has a laminar structure, the hot-adhesive will be formed from a thermoplastic polymer which has a lower melting point than at least one of the layers making up the laminar structure.

Examples of materials functioning as hot-melt adhesives include ethylene vinyl alcohol (EVA) and polyethylene, with EVA being preferred.

Where the outer bag and/or the backing sheet of the adhesive flange is of laminar structure and one or both of the contacting surfaces of the outer bag and backing sheet are formed from a thermoplastic polymer of the appropriate melting point, this can function as the hot-melt adhesive.

For example, in one embodiment, the outer bag is formed from a laminar film material comprising layers of EVA and polyvinyl dichloride (PVDC). In this embodiment, the EVA layer of the laminar film material can function as the hot-melt adhesive.

A preferred material for the backing sheet for the adhesive flange is polyurethane and it has been found that this material forms a particularly good peelable joint with an outer bag when the outer bag is formed from a laminar film comprising EVA/PVDC layers.

An adhesive bond between the backing sheet of the adhesive flange and the outer bag is typically formed by the application of heat using an appropriately shaped heat sealing tool. When EVA is used as the hot-melt adhesive, a temperature of about 120° C. to 160° C. is typically applied for a period of about 2 to 5 seconds.

The outer bag may have a sealed opening that can be opened to permit access to the interior thereof and removal and replacement of the inner bag. The sealed opening can be resealable after opening or can be non-resealable. In one embodiment, the sealed opening can be resealed after opening. An advantage of this arrangement is that the inner bag can be changed one or more times before the ostomy bag is judged to be ready for complete replacement.

The sealed opening in the outer bag may be formed in a number of ways. For example, the outer bag may comprise front and rear panels bonded together around their respective peripheries, but wherein a portion of the seam between the front and rear panels may be opened. Unless the context indicates otherwise, the term "front" as used herein refers to a panel or other portion of the bag which faces outwardly, i.e. away from the patient, whereas the term "rear" as used herein refers to a panel or other portion of the bag which faces inwardly, i.e. towards the patient.

The opening can be formed by partial opening of a seam between two panels of the outer bag, for example front and rear panels. The panels can be bonded together by Rf welding or by means of a non-peelable adhesive along a portion of the seam between the two panels and connected together by a peelable adhesive or by releasable mechanical interlocking means along another portion of the seam between the two panels. The releasable mechanical interlocking means can comprise, for example, interlocking ridges and grooves that form a releasable snap-fit connection between the panels, or a "Ziploc" type fastening extending around the seam, or releasable clamping means for holding the two panels together.

In one embodiment, a reinforced hinge mechanism may be employed. The hinge mechanism may comprise a pair of arcuate limbs linked together at both ends by living hinges, one of the arcuate limbs being bonded to the front panel of the outer bag and one being bonded to the rear panel of the outer bag. The length of the arcuate limbs can, for example, approximate to the arc of a semi-circle. The limbs are typically formed from a plastics material capable of forming a living hinge and thus withstanding repeated opening and closing without breaking. Examples of such materials include polypropylene, polyethylene and polyamides such as "Nylon".

In another embodiment, an opening (such as a "porthole") is formed in a panel (e.g. a front panel) of the bag, the opening being closed by a removable cover. The cover may be releasably secured about the opening by means of a peelable adhesive or by means of a mechanical interlocking means as described above.

In the drainage bags of the invention, the attachment zones for the inner and outer bags do not overlap, and, in this respect, the bags differ from the ostomy bags disclosed in US 2004/0059306 and WO 2004/082452, where the attachment zones for the inner and outer bags are shown as overlapping.

In the bags of the present invention, the first and second attachment zones may be contiguous or they may be spaced apart.

Where the first and second attachment zones are spaced apart, they may be spaced apart by a distance greater than the width of either attachment zone. It will be appreciated from this that when one attachment zone is wider than the other, the first and second attachment zones are spaced apart by a distance that is greater than the width of the widest of the two attachment zones.

In one embodiment, the first and second attachment zones may be spaced apart by a distance greater than one and half times the width of either attachment zone, or greater than twice the width of either attachment zone.

In a preferred embodiment of the invention, the first attachment zone has opposed inner edges and the lateral distance between the opposed inner edges along a line passing through the centre of the orifice is greater than the maximum lateral dimension of the inner bag.

The arrangement of the attachment zones for the outer and inner bags provides a number of advantages and these include greater ease of access to the interior of the outer bag for replacement of the inner bag and greater ease of manufacture.

The outer bag is typically formed from a waterproof material which acts as a barrier to flatus gases. Examples of such materials include polyvinyl dichloride (PVDC), ethylene vinyl alcohol and related materials and combinations thereof.

In order to prevent the undesirable build up of flatus gases within the bag, the wall of the outer bag can be provided with a flatus filter which permits gases to exit the bag but filters out malodorous and noxious gases. Such filters are well known and need not be described here.

The inner bag is detachably secured by means of adhesive to the second attachment zone on the flange. The adhesive is a peelable adhesive and may, for example, be a pressure sensitive adhesive or a non-pressure-sensitive adhesive. The peelable adhesive can be located on the second attachment zone, or on a ring surrounding the mouth of the inner bag, or on both. In one embodiment, the inner bag is provided with a ring of peelable adhesive surrounding the mouth of the bag.

The inner bag may be formed from a non-disposable waterproof material of a type described above for the outer bag, but preferably the inner bag is formed from a material that is biodegradable or disposable, such as polyvinyl alcohol. For example, the inner bag can be formed from a polymer, such as polyvinyl alcohol, of a type or grade that is slowly soluble in cold water but is more soluble in hot water. Examples of types of polyvinyl alcohol suitable for use in the fabrication of inner bags or liners are described in our earlier application WO94/12128.

DETAILED DESCRIPTION OF THE INVENTION

Figure 1:
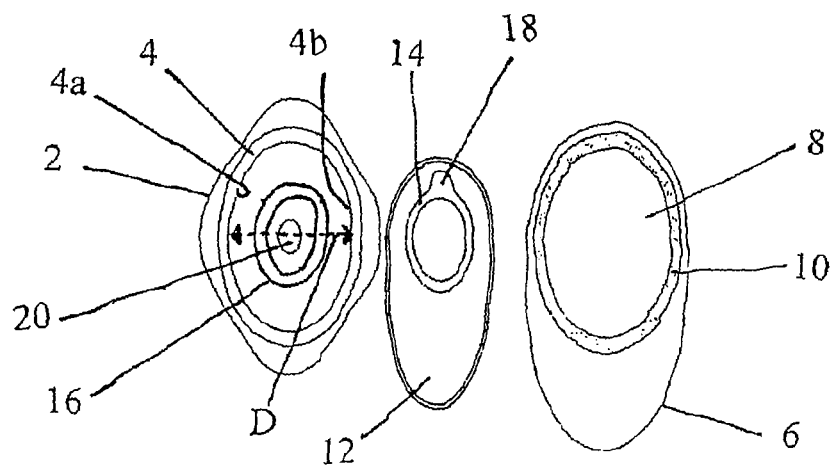
FIG. 1 is an exploded schematic view showing a flange, inner bag and outer bag of an ostomy bag according to one embodiment of the invention.

The invention will now be described in more detail, but not limited, by reference to the specific embodiments illustrated in the drawings.

Referring now to the Figures, FIG. 1 is an exploded schematic view showing the component parts of an ostomy bag according to the invention. The ostomy bag comprises an adhesive flange 2 comprising a backing layer of a polyurethane material to one side of which is attached a layer of hydrocolloid adhesive. The hydrocolloid adhesive, which may be of conventional type, serves to secure the ostomy bag to the body of a patient. A silicone release layer (not shown) covers the hydrocolloid adhesive layer and protects the adhesive layer against damage and/or drying out prior to use of the bag.

On the side of the flange opposite to the hydrocolloid adhesive is a first attachment zone designated in FIG. 1 by the numeral 4. An outer bag 6 having an opening 8 surrounded by a ring 10 of peelable but non-repositionable adhesive material is secured to the flange 2, the ring of peelable but non-repositionable adhesive 10 bonding to the flange at the first attachment zone 4. The peelable non-repositionable adhesive is a hot melt adhesive such as EVA. In the embodiment shown, the EVA can be a discrete layer applied only to the area of the ring 10. Alternatively, when the wall of the outer bag 6 is formed from an EVA/PVDC laminate or an EVA/PVDC/EVA laminate, the EVA layer of the laminate can function as the hot-melt adhesive.

The bond between the outer bag and the first attachment zone is formed by positioning the laminated film in the area of the attachment zone and applying heat with an annular heat sealing tool at a temperature of 120° C. to 160° C. for a period of 2 to 5 seconds.

When (as described below) the outer bag is subsequently peeled away from the outer attachment zone, it is not possible to reattach it to the attachment zone since the EVA does not have any significant adhesive capability at room temperature and pressure.

Disposed within the outer bag, is a removable inner bag or liner 12. The inner bag or liner 12 is provided with a ring of peelable adhesive 14, which bonds to the flange 2 at the second attachment zone 16. The ring of peelable adhesive 14 is provided with a tab 18 to facilitate removal of the inner bag from the flange.

The first attachment zone 4 and the second attachment zone 16 are spaced apart radially and the spacing between the two attachment zones is greater than the width of either of the two attachment zones. In the embodiment shown, the lateral distance D along a line running through the centre of the orifice 20 between opposed inner edges 4a and 4b of the first attachment zone is greater than the maximum lateral dimension of the inner bag 12.

The outer bag 6 in this embodiment can be formed from materials well known for the construction of ostomy bags. Thus, for example, it can be formed from a tough, flexible, transparent, waterproof material such as polyvinyl dichloride (PVDC), ethylene vinyl alcohol, related materials and combinations thereof in known fashion, one particular material being the EVA/PVDC/EVA film available from Sealed Air of Saddle Brook, N.J., US under the trade name Cryovac MF514. The outer bag may be formed from a pair of sheets of the flexible waterproof material, one sheet being cut so as to form the opening 8 and the other sheet having the same outer periphery, but no opening. The two sheets can be secured together around their respective peripheries by welding, (for example Rf welding) or by means of adhesive.

In use, fecal material from a stomal opening passes through the opening 20 in the flange and into the interior of the inner bag or liner 12. When the inner bag or liner 12 is full, the outer bag 6 may be peeled away from the flange, giving access to the inner bag, which may also be peeled away. The adhesive flange may also then be removed. The outer bag, adhesive flange and inner bag can then be disposed of, the inner bag and its contents by flushing down a WC and the outer bag and flange through normal domestic waste channels. A new assembly of inner and outer bag and adhesive flange may then be applied to the patient.

Figure 2:
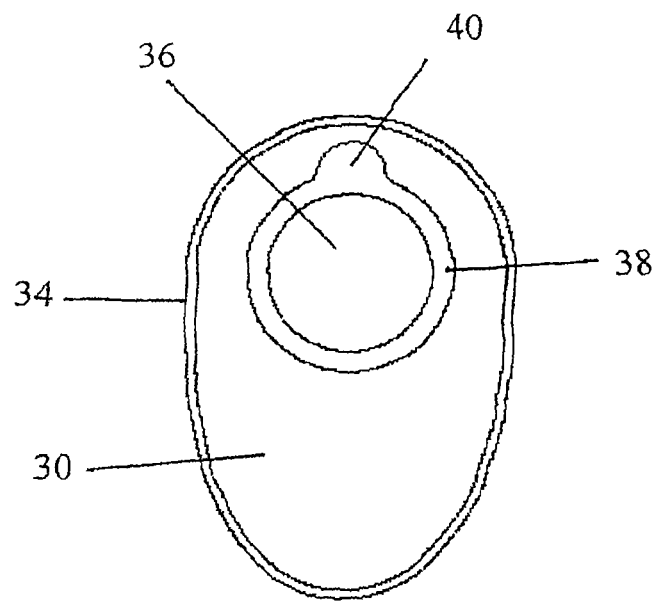
FIG. 2 illustrates a liner or inner bag for an ostomy bag.

An inner bag or liner is illustrated in more detail in FIG. 2 and comprises a pair of sheets, 30 and 32 (not shown) secured together by means of a weld 34 around their peripheries. The inner bag or liner 30 has an opening 36 surrounded by a ring of a peelable adhesive 38, covered by a silicone release layer (not shown). A tab 40 assists in removal of the liner from the flange. The inner bag 30 may be formed from a non-disposable waterproof material such as polyvinyl dichloride or a PVDC/EVA laminate, or another material similar to the materials from which the outer bag is made. Alternatively, the inner bag can be formed from materials that are biodegradable or disposable. Examples of materials suitable for forming a disposable liner are described in our earlier patent application WO94/12128 and include polyvinyl alcohol of an appropriate solubility grade.

Figure 3:
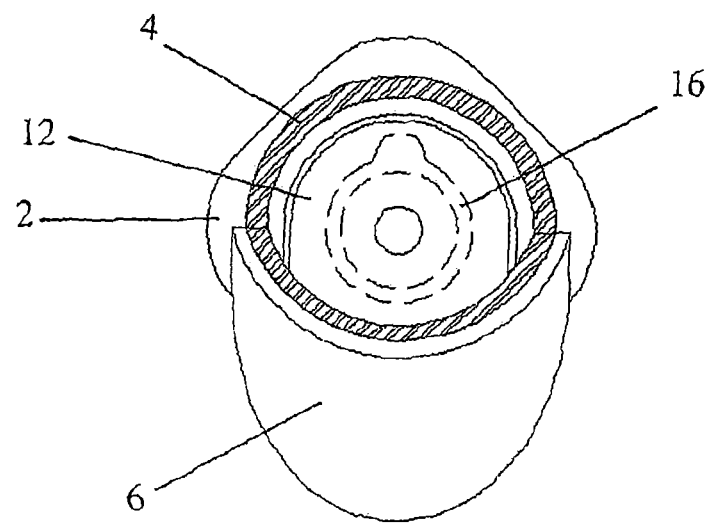
FIG. 3 illustrates an ostomy bag in which the outer bag has been partially peeled away to reveal the inner bag.

The layout of the inner and outer bags and their respective attachment zones in the assembled ostomy bag can be seen more clearly in FIG. 3 which illustrates an ostomy bag in which the outer bag 6 has been partially peeled away to reveal the bag interior and the inner bag 12.

Figure 5:
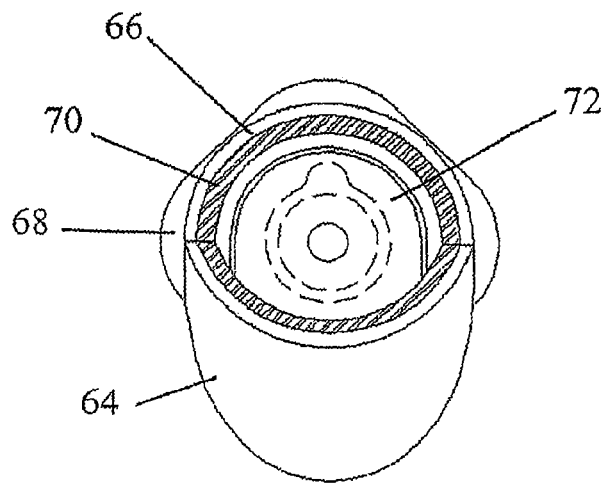
FIG. 5 illustrates an outer bag with an opening along its edge seam.

In the embodiment shown in FIG. 5, the outer bag comprises front 64 and rear panels 66, the rear (i.e. body-side) surface of rear panel 66 being bonded by non-peelable adhesive or by Rf welding around its entire periphery to the adhesive flange 68. The front panel 64 is permanently bonded to the rear panel along part of its periphery but is releasably attached to the rear panel along the remainder of its periphery by means of the line of peelable adhesive 70. Thus, in this embodiment, the seam between the front and drear panels opens up to give access to the interior of the bag for removal of the inner bag or liner 72.

Figure 4:
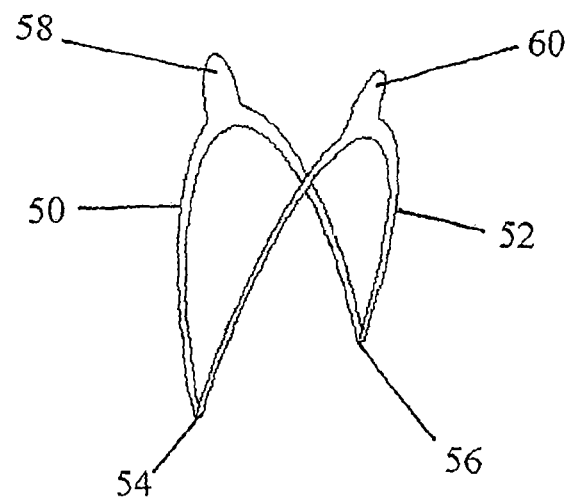
FIG. 4 illustrates a hinge mechanism for use in an opening in an outer bag.

In order to provide a firmer engagement and disengagement action between the two panels of the outer bag, a hinge mechanism may be interposed between the panels and one such mechanism is shown in FIG. 4. The hinge mechanism illustrated in FIG. 4 comprises a pair of generally semicircular limbs 50 and 52, linked together by living hinges 54 and 56. Tabs 58 and 60 are provided to assist the user to pull the two limbs apart. The limb 52 of the hinge mechanism can be secured to rear panel 66 of the bag shown in FIG. 5, for example by Rf welding, whilst the second limb 50 of the hinge can be secured (again by Rf welding or adhesive) to the front panel 64 of the outer ostomy bag. The confronting surfaces of the two limbs may be provided with a peelable adhesive to allow them to be releasable secured together, or they may be provided with a mechanical fastening mechanism.

Figure 6:
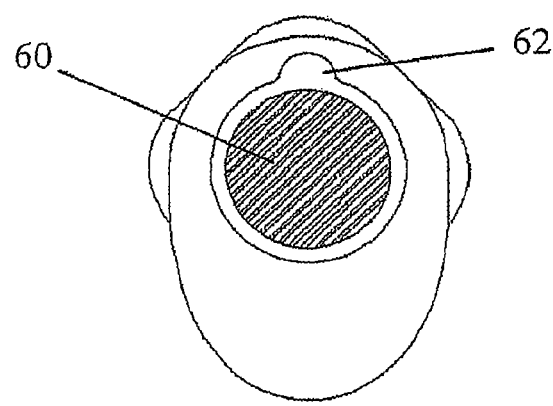
FIG. 6 illustrates an outer bag with a porthole to provide access to the inner bag.

In a further form of construction, a panel or wall of the outer bag may be provided with an opening to allow access to the replaceable inner bag or liner. FIG. 6 illustrates an embodiment in which a "porthole" is created in the outer bag wall, and a cover 60 is secured in place by a ring of adhesive around its periphery. A tab 62 is provided to assist in removal of the porthole cover.

Figure 7A:
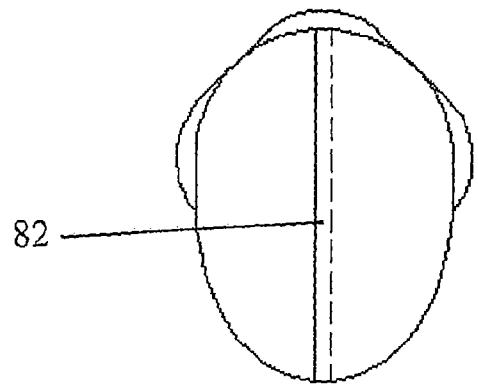
FIGS. 7a and 7b illustrate an opening in an outer bag of an ostomy bag according to another embodiment of the invention.
Figure 7B:
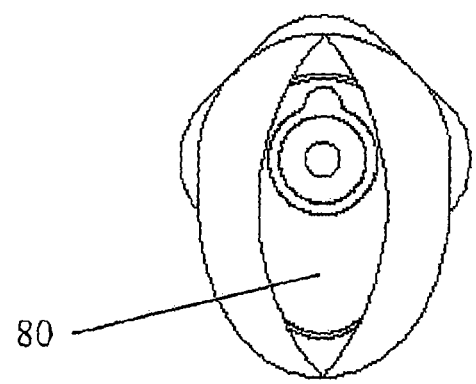

In a further alternative, as shown in FIGS. 7a and 7b, an opening may be formed in the outer bag along a seam, the opening being closed by a temporary closure mechanism, such as a clip and folding mechanism using, for example, a physical interlocking system such as a closure of the "Ziploc®" type, or hook and loop systems of the "Velcro®" or Cric Crac® type, or interlocking "mushroom" fasteners of the type manufactured by Gottlieb Binder GmbH of Holzgerlingen, Germany. Particular fasteners of interest include fasteners that provide a substantially water-tight closure.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. A drainage bag assembly for receiving bodily waste; the drainage bag assembly comprising:
   an outer bag and an inner bag secured to one side of a flange, the flange being provided with means defining an orifice to enable bodily waste to be received by the inner bag, and the flange having connected to an opposite side thereof means for securing the drainage bag assembly to the body of a patient;
   the outer bag being detachably secured by means of a peelable but non-repositionable adhesive to a first attachment zone on the flange and the inner bag being detachably secured by means of a peelable adhesive to a second attachment zone on the flange, wherein the first attachment zone entirely surrounds the second attachment zone and is non-overlapping therewith; and the second attachment zone surrounds the means defining the orifice; and wherein the outer bag can be removed or opened to permit access to the interior thereof and removal of the inner bag.

2. The drainage bag assembly of claim 1, wherein the peelable but non-repositionable adhesive is a hot melt adhesive.

3. The drainage bag assembly of claim 2, wherein the hot melt adhesive is at least one of polyethylene or ethylene vinyl alcohol.

4. The drainage bag assembly of claim 3, wherein the hot melt adhesive is ethylene vinyl alcohol.

5. The drainage bag assembly of claim 1, wherein the outer bag has a wall which is of laminar structure, and wherein the peelable but non-repositionable adhesive is a hot melt adhesive which is constituted by a layer of the laminar structure.

6. The drainage bag assembly of claim 1, wherein the first and second attachment zones are contiguous.

7. The drainage bag assembly of claim 1, wherein the first and second attachment zones are spaced apart.

8. The drainage bag of claim 7, where the first and second attachment zones are spaced apart by a distance greater than the width of either attachment zone.

9. The drainage bag of claim 8, wherein the first and second attachment zones are spaced apart by a distance greater than one and half times the width of either attachment zone.

10. The drainage bag of claim 1, wherein the first attachment zone has opposed inner edges, the lateral distance between the opposed inner edges along a line passing through the centre of the orifice being greater than the maximum lateral dimension of the inner bag.

11. The drainage bag of claim 1, wherein the means for securing the drainage bag assembly to the body of a patient comprises a layer of adhesive.

12. The drainage bag of claim 1, wherein the outer bag is formed from front and rear panels secured together around their respective peripheries, a portion of a seam between the pair of panels at the peripheries thereof being openable to permit access to and replacement of the inner bag.

13. The drainage bag of claim 1, wherein an opening is formed in a panel of the outer bag, the opening being closed by a removable and replaceable cover.

14. The drainage bag of claim 13, wherein the cover is releasably secured about the opening by means of a peelable adhesive or a mechanical interlocking means.

15. The drainage bag of claim 1, wherein the inner bag is formed from a biodegradable material or a material that disintegrates when exposed to water.

16. The drainage bag of claim 1, wherein the flange comprises a backing layer formed from a polymeric material, to one side of which is attached the means for securing the drainage bag assembly to the body of a patient, and to the other side of which are attached the outer and inner bags, and wherein the peelable but non-repositionable adhesive has a melting point at least 20° C. lower than the melting point of the said polymeric material.

17. The drainage bag of claim 16, wherein the polymeric material is polyurethane.

18. The drainage bag of claim 16 wherein the means for securing the drainage bag assembly to the body of a patient is a layer of adhesive.

19. The drainage bag of claim 1 which is an ostomy bag.

20. The drainage bag of claim 11, wherein the layer of adhesive is a hydrocolloid adhesive.

21. The drainage bag of claim 18, wherein the layer of adhesive is a hydrocolloid adhesive.

22. A drainage bag assembly for receiving bodily waste; the drainage bag assembly comprising:
   an outer bag and an inner bag secured to one side of a flange, the flange being provided with means defining an orifice to enable bodily waste to be received by the inner bag, and the flange having connected to an opposite side thereof means for securing the drainage bag assembly to the body of a patient;

the outer bag being detachably secured by means of a peelable but non-repositionable adhesive to a first attachment zone on the flange and the inner bag being detachably secured by means of a peelable adhesive to a second attachment zone on the flange, wherein the first attachment zone entirely surrounds the second attachment zone and is non-overlapping therewith; and the second attachment zone surrounds the means defining the orifice, wherein the outer bag can be removed or opened to permit access to the interior thereof and removal of the inner bag;

wherein the outer bag is formed from front and rear panels secured together around their respective peripheries, a portion of a seam between the pair of panels at the peripheries thereof being openable to permit access to and replacement of the inner bag;

wherein a living hinge mechanism is disposed between the panels in the openable portion of the seam, the living hinge mechanism providing a reclosable opening for the outer bag and comprising a pair of hinge limbs linked together at the two ends of each hinge limb by living hinges so as to define a reclosable opening, with one of the hinge limbs being attached to a front panel of the outer bag and the other hinge limb being attached to the flange or a rear panel of the outer bag, the two hinge limbs being provided with releasable securing means on confronting surfaces thereof for holding the limbs together to close the opening.

23. The drainage bag of claim 22, wherein the hinge limbs are arcuate.

* * * * *

UNITED STATES PATENT AND TRADEMARK OFFICE
CERTIFICATE OF CORRECTION

| | | |
|---|---|---|
| PATENT NO. | : 8,740,832 B2 | Page 1 of 1 |
| APPLICATION NO. | : 12/522509 | |
| DATED | : June 3, 2014 | |
| INVENTOR(S) | : Smith et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1470 days.

Signed and Sealed this
Twenty-eighth Day of July, 2015

Michelle K. Lee
*Director of the United States Patent and Trademark Office*